(12) United States Patent
Wu et al.

(10) Patent No.: US 7,408,080 B2
(45) Date of Patent: Aug. 5, 2008

(54) PROCESS FOR AMMOXIMATION OF CARBONYL COMPOUNDS

(75) Inventors: Wei Wu, Beijing (CN); Bin Sun, Beijing (CN); Yongxiang Li, Beijing (CN); Shibiao Cheng, Beijing (CN); Enquan Wang, Beijing (CN); Shuzhong Zhang, Beijing (CN)

(73) Assignees: China Petroleum & Chemical Corporation, Beijing (CN); Research Institute of Petroleum Processing, Sinopec, Beijing (CN)

( * ) Notice: Subject to any disclaimer, the term of this patent is extended or adjusted under 35 U.S.C. 154(b) by 1238 days.

(21) Appl. No.: 10/448,282

(22) Filed: May 30, 2003

(65) Prior Publication Data

US 2005/0215810 A1    Sep. 29, 2005

(30) Foreign Application Priority Data

May 31, 2002    (CN) .............................. 02 1 20783

(51) Int. Cl.
*C07C 249/04* (2006.01)
(52) U.S. Cl. .................. 564/253; 564/259; 564/262
(58) Field of Classification Search .............. None
See application file for complete search history.

(56) References Cited

U.S. PATENT DOCUMENTS

| 4,396,783 A | 8/1983 | Esposito et al. |
| 4,410,501 A | 10/1983 | Taramasso et al. |
| 4,480,135 A | 10/1984 | Esposito et al. |
| 5,227,525 A | 7/1993 | Tonti et al. |
| 5,312,987 A | 5/1994 | Mantegazza et al. |
| 5,498,793 A | 3/1996 | Mantegazza et al. |
| 6,828,459 B2 * | 12/2004 | Oikawa et al. ............... 564/253 |
| 7,067,699 B2 * | 6/2006 | Oikawa et al. ............... 564/267 |

FOREIGN PATENT DOCUMENTS

| CN | 1097151 | 1/1995 |
| CN | 1345718 | 4/2002 |
| CN | 1367166 | 9/2002 |
| EP | 0208311 | 1/1987 |
| EP | 0230949 | 8/1987 |
| EP | 0267362 | 5/1988 |
| EP | 0347926 | 12/1989 |
| EP | 0384390 | 8/1990 |
| EP | 0496385 | 7/1992 |
| EP | 0564040 | 10/1993 |

OTHER PUBLICATIONS

J. Le Bars et al., Applied Catalysis A, vol. 136 (1996) p. 69-80.
Peng Wu et al., Journal of Catalysis, (1997) vol. 168, p. 400-411.
G. Petrini et al. Catalyst Deactivation vol. 68 (1991), p. 761-766.
Selective Oxidation by Heterogeneous Catalysis, 2001, p. 108-113.

* cited by examiner

*Primary Examiner*—Brian J Davis
(74) *Attorney, Agent, or Firm*—Scully, Scott. Murphy & Presser, P.C.

(57) ABSTRACT

The present invention discloses a process for the ammoximation of carbonyl compounds, wherein a reaction in a liquid reaction system comprising a carbonyl compound, ammonia and hydrogen peroxide is carried out in the presence of a sillicon-containing catalyst, characterized in that a liquid silicon-containing assistant is added to the reaction system so that the silicon concentration in the system reaches a range of between 0.1 and 10000 ppm. In the process according to the present invention, the deactivation of catalyst due to dissolution of silicon in the catalyst can be reduced, thus lifetime of the catalyst extended and the stable operation time elongated.

14 Claims, No Drawings

PROCESS FOR AMMOXIMATION OF CARBONYL COMPOUNDS

TECHNICAL FIELD

The present invention relates to a process for ammoximation of carbonyl compounds.

BACKGROUND ART

Carbonyl compounds refer to compounds having >C=O function group, such as aldehydes or ketones. The reaction of carbonyl compound with hydroxylamine is a main process for the syntheses of the corresponding oxime compound.

For example, in the case of cyclohexanone oxime, cyclohexanone oxime is a key intermediate for producing ε-caprolactam which is an important raw material in organic chemical industry mainly used as a monomer for synthetic fibers and-engineering plastics (e.g., nylon-6). About 91% of caprolactam are produced industrially via a technique route with cyclohexanone oxime as intermediate product, in which cyclohexanone oxime is produced by the reaction of cyclohexanone with hydroxylamine (used in its sulfate or phosphate form). This process for the production of cyclohexanone oxime has a complex technology with multiple process steps and high investment in equipment, and it also has a problem in corrosion and pollution due to use or production of NOx, SOx and the like.

In the early 1980's, in U.S. Pat. No. 4,410,501, Taramasso (Italy) disclosed a novel type of catalyst material—titanium silicalite having an excellent function for selective oxidation of hydrocarbons, alcohols, phenols and the like (EP 0230949, U.S. Pat. No. 4,480,135, U.S. Pat. No. 4,396,783). It has been commercialized to use it for the preparation of catechol and hydroquinone by the selective oxidation of phenol with hydrogen peroxide.

EP 0208311, EP 0267362, EP 0496385, EP 0564040, etc. sequentially disclose a novel process for preparing cyclohexanone oxime in one step by ammoximation of cyclohexanone with ammonia and hydrogen peroxide catalyzed by titanium silicalite. This novel process features in mild reaction conditions, high yields of desired products, more efficient process, lower investment in equipment, reduced amount of wastes and environmental friend.

Furthermore, EP0347926 discloses that the ammoximation of cyclohexanone is carried out by using a catalyst in which titanium dioxide is dispersed on silica, also exhibiting a relatively good catalytic performance; both J. Le. Bars et al., Appl. Catal. A 136(1996) p. 69 and P. Wu et al., J. Catal. 168 (1997) p. 400 report that other types of Ti-containing crystalline silicate, such as Ti-ZSM-48, Ti-β, Ti-MOR and the like, which all exhibit relatively good catalytic performance for the ammoximation of a variety of aldehyde or ketone compounds.

As the ammoximation of cyclohexanone is investigated intensively in preparing cyclohaxnone oxime, deactivation of various titanium-containing catalysts, mainly titanium silicalites, in this reaction has been increasingly focused.

EP 0496385 discloses that it is necessary to remove off the deactivated catalyst periodically, which is to be replaced by a fresh catalyst make-up in order to maintain the desired catalytic activity during the reaction.

U.S. Pat. No. 5,498,793 discloses a process for the production of oximes which comprises ammoximation of a carbonylic compound selected from acetophenone and cyclododecanone with hydrogen peroxide and ammonia in the presence of a catalyst based on silicon, titanium and oxygen and a cocatalyst consisting of amorphous silica. The cocatalyst added in the said process can increase the yields and conversions in the ammoximation of acetophenone and cyclododecanone, but does not solve the deactivation of the main catalyst.

CN1345718A discloses a process for preparing oxime from carboxyl compound, hydrogen peroxide and ammonia, involving the addition of cocatalyst containing acidic solid into the reaction system so as to increase the conversion rate of the ammoximation of the carbonyl compound. However, the acidic solid cocatalyst added in the said process does not solve the deactivation of the main catalyst.

G. Petrini et al., Stud. Surf. Sci. Catal. 68(1991) p. 761 identifies the three main deactivation processes of titanium silicalites in the ammoximation of cyclohexanone: (1) slow dissolution of the framework (silicon) with accumulation of Ti on the external surface of the remaining solid, (2) direct removal of Ti from the framework and (3) pore filling by by-products. The first two are due to the basic reaction medium in the presence of ammonia, which results in silicon dissolution away from the titanium silicalite framework. Since only Si is removed from and Ti remains in the catalyst, Ti content of the catalyst relatively increases and the degree of crystallinity of the catalyst tends to decrease. The literature further shows that, although there is only a small amount of silicon (ppm) dissolved in the reaction stream, the silicon dissolution during the long term running will result in a continuous decrease in the amount of the titanium silicalites in the reaction system. The weight of catalyst recovered will be lower than that of the starting one. Under extreme conditions, the recovery of catalyst is 35% only.

In the book *Selective Oxidation by Heterogenous Catalysis* (2001, p. 112), it is shown that dissolution of silicon in Ti-containing crystalline silicas caused by ammonia is the primary factor leading to deactivation of the catalyst during ammoximation of cyclohexanone. Since ammonia is an indispensable raw material in the ammoximation of cyclohexanone, the problem caused thereby is inevitable. Although this problem has been confirmed, no relevant technical solutions solving the problem have been reported yet. Similar problem is also present in reaction systems of ammoximation of other aldehydes and ketones.

In the ammoximation of carbonyl compounds mentioned above, the dissolution loss of silicon from the catalysts will result in disadvantageous effects, such as reducing the stable operation time of catalyst and decreasing the recovery of catalyst. Nevertheless, although the silicon dissolution in the Ti-containing crystalline silicas caused by ammonia is the primary factor for the deactivation of catalyst, adding into the system the acidic solids, such as solid silica gel, as stated in CN1345718A cannot solve the problem as to the deactivation of catalyst.

DESCRIPTION OF THE INVENTION

An object of the present invention is directed to the deficiency of the prior arts to provide a process for the ammoximation of carbonyl compounds, which is able to delay the deactivation of catalyst, prolong the stable operation time of the catalyst and increase the recovery of the catalyst.

The present invention provides a process for the ammoximation of carbonyl compounds, wherein the reaction in a liquid reaction system comprising a carbonyl compound, ammonia and hydrogen peroxide is carried out in the presence of a silicon-containing catalyst, characterized in that a liquid silicon-containing assistant is added to the reaction system so that the silicon concentration in the medium reaches a range of between 0.1 and 10000 ppm. Preferably, the silicon concentration reaches an equilibrium dissolution concentration of silicon in the solution.

Said carbonyl compound is one selected from the group consisting of cyclohexanone, acetone, butanone, cyclopentanone, acetophenone, p-hydroxylacetophenone, cyclododecanone, furfural, benzaldehyde, and p-methylbenzaldehyde.

Said silicon-containing catalyst refers to a crystalline silica or a metal-dispersed silica catalyst, wherein said crystalline silica may be used in the form of its original powder or its molded form. In said crystalline silica, titanium-containing crystalline silica, such as TS-1, TS-2, Ti-ZSM-5, Ti-ZSM-12, Ti-ZSM-48, Ti-1β, Ti-MCM-41, Ti-MOR, or the like, is preferred. More preferably, said crystalline silica is TS-1 (titanium silicalite-1) having the MFI structure.

No matter the silicon-containing catalyst is the amorphous silica or the crystalline silicate with different structure, silicon can be dissolved in the ammonia-containing medium in either case and reaches an equilibrium concentration. However, this equilibrium concentration varies in a great range (from 0.1 to several thousand ppm) as the medium varies. The present inventors surprisingly discover that, if a liquid silicon-containing substance is added in the reaction system, the liquid silicon-containing substance can firstly be dissolved in the medium, and the silicon-containing catalyst is hardly dissolved.

In the process of the present invention, the said liquid silicon-containing assistant may be in liquid forms such as sol, solution, suspension or emulsion, etc. It can firstly be dissolved in the reaction system, such that the silicon-containing catalyst is hardly dissolved. The state of the raw material of the said liquid silicon-containing assistant is not restricted, which implies that it can be any of gas, liquid or solid state. But, when being added to the system, the silicon-containing raw material should be in a liquid form, such as sol, solution, suspension or emulsion, etc. Said liquid silicon-containing assistant is preferably in the liquid form of sol or solution.

Said silicon-containing assistant is selected from various inorganic silicon-containing substances or various organic silicon-containing substances. Said inorganic silicon-containing substances include silicas or silicates; said silicates include sodium silicate, potassium silicate, aluminum silicate etc.; said organic silicon-containing substances are selected from silicate esters or silanes, said silicate ester is preferably ethyl silicate.

In the process of the present invention, said liquid silicon-containing assistant is added to the reaction system in an amount sufficient to make the silicon content in the reaction medium reach a range of from 0.1 to 10000 ppm. Preferably, the amount of the assistant added should make the silicon content reach an equilibrium dissolution concentration of silicon in the reaction medium. Due to the difference in composition of the reaction system (e.g. solvent, concentration of ammonia etc.), the equilibrium concentration of silicon in the system is varied. For example, in a reaction system with t-butanol-water solvent, the equilibrium dissolution concentration of silicon in the system is between 10 and 100 ppm. But in an aqueous reaction system, the equilibrium dissolution concentration of silicon is between 1000 and 3000 ppm. In addition, in the process of the present invention, said silicon-containing substances may be added continuously or in batch, preferably continuously.

In the process for the ammoximation of carbonyl compounds according to the present invention, based on the dissolution of silicon in a basic solution, a step of adding a liquid silicon-containing assistant is adopted in the ammoximation of carboyl compounds. In this case, the dissolution of silicon from the catalyst can be inhibited, and the destruction of ammonia to the catalyst is thus reduced Due to the concentration of the catalyst in the reaction system maintained, and the deactivation of the catalyst caused by the dissolution of silicon from the catalyst decreased, the lifetime of the catalyst is prolonged and the stable operation time is increased. For example, in the case of the ammoximation of cyclohexanone catalyzed by TS-1, from the results of analysis and characterization of the TS-1 recovered from the process according to the present invention, it can been seen that no changes occur in the TS-1 as to the degree of crystallinity and Ti content, as compared with a fresh catalyst. However, for the reaction systems in which no silicon-containing assistant is added or a silicon-containing substance is added only in the form of solid, the deactivated catalyst obtained after a period of running can be seen changed. Its Ti content is relatively increased due to the dissolution of silicon from catalyst and the retention of titanium in the catalyst. Simultaneously, a tendency to decrease of the degree of crystallinity of the catalyst occurs.

EXAMPLES

The following examples are given to further illustrate the present invention, but not to limit the invention in any way.

In the examples and comparative examples hereinbelow, the following materials were used: titanium silicalite-1 (TS-1) manufactured by Yueyang Jianchang Corp. Ltd., Human province, China; cyclohexanone ($\geqq$99.5% in purity) available from Beijing Chemical Factory, Beijing, China; hydrogen peroxide solution (containing 27.5% by weight of $H_2O_2$) available from Tianjin Dongfang Chemical Factory, Tianjin, China ammonia ($\geqq$99.9% in purity) available from Beijing Experiment Chemical Factory, Beijing, China; t-butanol (containing 86.5% by weight of t-butanol and the balance of water and a small quantity of impurities) available from Beijing Pingshun Chemical Industry Corp Ltd., Beijing, China; and silica sol produced by Qingdao Ocean Chemical Factory, Shandong province, China. Unless otherwise specially stated, all the other chemical reagents were products with chemical purity grade available from Beijing Chemical Factory, Beijing, China.

In these examples, the reaction products were analyzed for compositions with gas chromatography and the conversion rate of hydrogen peroxide was obtained by measuring its content with Iodimetry. Ti content of the catalyst and silicon content in the reaction system were measured with inductively coupled plasma-atomic emission spectrascopy (ICP-AES). The degree of crystallinity of crystalline silica was measured with X-ray diffraction spectrometry (XRD).

Example 1

In this example, cyclohexanone oxime was prepared by ammoximation of cyclohexanone, TS-1 was used in its original powder form as the catalyst.

150-ml autoclave equipped with a magnetic stirrer and an oil-bath heater was used. Reaction feedstocks and reaction products flow in or out of the reactor continuously, and TS-1 was retained in the autoclave.

Reaction conditions were as follows: $H_2O_2$:cyclohexanone=1.10:1 mol/mol; ammonia:cyclohexanone=1.70:1 mol/mol; t-butanol:cyclohexanone=3.30:1 mol/mol, the silicon content in the reaction medium=35 ppm, the catalyst concentration was 1.8% by weight, an average residence time of the reaction stream was 72 min., the reaction temperature was 76±1° C., the reaction pressure was atmospheric pressure, silica sol was added continuously as a silicon-containing assistant. Reaction results are shown in Table 1, where the stable operation time of catalyst is based on a one-way running period in which ≧97% of the conversion of cyclohexanone is obtained.

Comparative Example 1

Example 1 was repeated, except that no silica sol was added. Reaction results are shown in Table 1.

Comparative Example 2

Example 1 was repeated, except that no silicon-containing assistant was added continuously during the reaction. Instead, acidic silica gel solid was added in one stock, which is used in a weight ratio to the catalyst (TS-1) of 0.4:1. Reaction results are shown in Table 1.

Example 2

Example 1 was repeated, except that toluene was used as the solvent instead of t-butanol, tetraethyl orthosilicate (Beijing Chemical Reagents Corp., Beijing, China) was added in aqueous solution, and the silicon content in the reaction medium was 1035 ppm. Reaction results are shown in Table 1.

Example 3

Example 1 was repeated, except that the reaction temperature was 83±1° C., the reaction pressure was 0.3 MPa, the catalyst concentration was 2.0% by weight, the molar ratio of $H_2O_2$/cyclohexanone was 1.08:1 and the silicon content in the reaction medium was 100 ppm. Reaction results are shown in Table 2, where the stable operation time of catalyst is based on an one-way running period in which ≧97% of the conversion of cyclohexanone is obtained.

Comparative Example 3

Example 3 was repeated, except that no silicon-containing assistant was added. Reaction results are shown in Table 2.

TABLE 1

| No. | Comp. Ex. 1 | Comp. Ex. 2 | Ex. 1 | Ex.2 |
|---|---|---|---|---|
| silicon-containing assistant | — | Acidic silica gel solid | Silica sol | tetraethyl orthosilicate |
| Results | | | | |
| Conversion of cyclohexanone, % | 98.5 | 98.5 | 98.6 | 98.5 |
| Conversion of $H_2O_2$, % | 100 | 100 | 100 | 100 |
| Selectivity of cyclohexanone to cyclohexanone oxime, % | 99.6 | 99.6 | 99.7 | 99.5 |
| Selectivity of $H_2O_2$ to cyclohexanone oxime, % | 89.2 | 89.2 | 89.4 | 89.1 |
| Stable operation time, h | 40 | 42 | 65 | 60 |
| Recovery of catalyst (calcined), wt % | 87.7 | 88.5 | 98.7 | 97.8 |
| Charaterized results of catalyst | | | | |
| Ti content (relative to fresh catalyst), % | 106.8 | 106.0 | 99.5 | 101.1 |
| Degree of crystallinity (relative to fresh catalyst), % | 99 | 99 | 100 | 100 |

TABLE 2

| No. | Comp. Ex. 3 | Ex. 3 |
|---|---|---|
| silicon-containing assistant kind | — | Silica sol |
| Results | | |
| Conversion of cyclohexanone, % | 99.5 | 99.5 |
| Conversion of $H_2O_2$, % | 100 | 100 |
| Selectivity of cyclohexanone to cyclohexanone oxime, % | 99.6 | 99.7 |
| Selectivity of $H_2O_2$ to cyclohexanone oxime, % | 91.8 | 91.9 |
| Stable operation time, h | 100 | 210 |
| Recovery of catalyst (calcined), wt % | 80.3 | 102.8 |
| Charaterized results of catalyst | | |
| Ti content (relative to fresh catalyst), % | 113.1 | 98.6 |
| Degree of crystallinity (relative to fresh catalyst), % | 97 | 100 |

Tables 1 and 2 reveal that, no influence on the activity and selectivity of catalyst is observed after adding the silicon-containing sol or solution, the stable operation time are obviously elongated in comparison with that in the comparative examples, and the recovery of catalyst is higher than 97% by weight; furthermore, the deactivated catalyst has no change in the degree of crystallinity and Ti content in comparison with the fresh catalyst. In the comparative examples, however, no silicon-containing sol or solution is added (comparative examples 1 and 3) or the silicon-containing substance is added to the system only in the form of solid (comparative example 2), Ti content of the deactivated catalyst obtained after a period of running is relatively increased due to the dissolution of silicon from and the retention of titanium in the catalyst. Simultaneously, a tendency to a decrease of the degree of crystallinity of the molecular sieve occurs.

Examples 4 to 7

In Examples 4 to 7, the ammoximation process was carried out by reacting acetone, cyclopentanone, benzaldehyde, p-methylbenzaldehyde as the feedstocks carbonyl compounds respectively with ammonia and hydrogen peroxide in the presence of Ti-MOR (Si/Al=300, prepared with the process recited in J. Catal. 168(1997) p. 400) as the catalyst, wherein water was used as the solvent, and silica sol was added. The reaction conditions were as follows: $H_2O_2$:ketone (aldehyde)=1.15:1 mol/mol, ammonia:ketone (aldehyde) =2.0:1 mol/mol, water:ketone (aldehyde)=8:1 vol/vol, the catalyst concentration was 3.0 wt %, the average reaction residence time of stream was 120 min., the reaction temperature was 60±1° C. and the reaction pressure was atmospheric pressure.

Reaction results are shown in Table 3, where the stable operation time of the catalyst is based on a one-way running period in which ≧90% of the conversion of aldehyde or ketone is obtained.

TABLE 3

| No. | Ex. 4 | Ex. 5 | Ex. 6 | Ex. 7 |
|---|---|---|---|---|
| Carbonyl compound | acetone | Cyclopentanone | Benzaldehyde | p-methyl benzaldehyde |
| Content of Si in reaction medium, ppm | 150 | 450 | 520 | 600 |
| Relative stable operation time (compared with that without silicon-containing assistant added) % | 155 | 140 | 130 | 145 |
| Recovery of catalyst (calcined), wt % | 98.5 | 97.2 | 96.5 | 97.9 |

Using the process according to the present invention, it can be seen from Table 3 that after silica sol is added, no influence is observed on the activity and selectivity of the catalyst. The conversion of Carbonyl compound is more than 90%, the selectivity to oxime is in the range of 95-99.5%, the stable operation time of the catalyst is obviously prolonged as compared with that with no silica sol added. And the recovery of the catalyst is more than 96% by weight.

Example 8

The reaction of cyclohexanone with ammonia and hydrogen peroxide was carried out by using Ti-supported silica as the catalyst (prepared in a way similar to Example 6 in EP 0 347 926) under the same reaction conditions as Example 1. After silica sol was added, no influence was observed on the activity and selectivity of the catalyst, but the stable operation time of the catalyst was elongated 30% relative to the catalyst with no silica sot added, and the recovery rate of the catalyst was 97% by weight.

The present application claims priority under 35 U.S.C. §119 of Chinese Patent Application No. 02120783.6 filed on May 31, 2002. The disclosure of the foregoing application is expressly incorporated by reference herein in its entirety.

The invention claimed is:

1. A process for the ammoximation of carbonyl compounds, wherein a reaction in a liquid reaction system comprising a carbonyl compound, ammonia and hydrogen peroxide is carried out in the presence of a sillicon-containing catalyst, characterized in that a liquid sillicon-containing assistant is added to the reaction system so that the silicon concentration in the system reaches a range of between 0.1 and 10000 ppm.

2. The process according to claim 1, characterized in that said carbonyl compound is one selected from the group consisting of cyclohexanone, acetone, butanone, cyclopentanone, acetophenone, p-hydroxyacetophenone, cyclododeconone, furfural, benzaldehyde and p-methylbenzaldehyde.

3. The process according to claim 1, characterized in that said sillicon-containing catalyst is selected from the group consisting of a crystalline silica or a metal-dispersed silica catalyst.

4. The process according to claim 3, characterized in that said crystalline silica is titanium-containing crystalline silica.

5. The process according to claim 4, characterized in that said titanium-containing crystalline silica is one selected from the group consisting of TS-1, TS-2, Ti-ZSM-5, Ti-ZSM-12, Ti-ZSM-48, Ti-β, Ti-MCM-41 and Ti-MOR.

6. The process according to claim 1, characterized in that said sillicon-containing assistant is selected from the group consisting of inorganic sillicon-containing substances or organic sillicon-containing substances.

7. The process according to claim 6, characterized in that said inorganic silicon-containing substance is selected from the group consisting of silica and silicates.

8. The process according to claim 7, characterized in that said silicate is selected from the group consisting of sodium silicate, potassium silicate and aluminum silicate.

9. The process according to claim 6, characterized in that said organic sillicon-containing substance is selected from the group consisting of silicate esters and silanes.

10. The process according to claim 9, characterized in that said silicate ester is ethyl silicate.

11. The process according to claim 1, characterized in that said liquid sillicon-containing assistant is added in an amount sufficient to make the silicon concentration in the reacting solution reach the equilibrium dissolution concentration of silicon in the solution.

12. The process according to claim 1, characterized in that said liquid sillicon-containing assistant is added continuously or in batch.

13. The process according to claim 12, characterized in that said liquid sillicon-containing assistant is added continuously.

14. The process according to claim 1, characterized in that said liquid silicon-containing assistant is silica sol or a silicon-containing solution.

* * * * *